US012799656B2

(12) United States Patent
Padia et al.

(10) Patent No.: US 12,799,656 B2
(45) Date of Patent: Nov. 17, 2026

(54) CLOTHES PRE-WASHING DEVICE AND METHOD THEREOF

(71) Applicant: HCL Technologies Limited, New Delhi (IN)

(72) Inventors: Neel Paresh Padia, Bengaluru (IN); Vijaya VN, Bengaluru (IN); Himanshu Sunil Laddha, Bengaluru (IN); Dipumon AM, Bengaluru (IN)

(73) Assignee: HCL Technologies Limited, New Delhi (IN)

( * ) Notice: Subject to any disclaimer, the term of this patent is extended or adjusted under 35 U.S.C. 154(b) by 101 days.

(21) Appl. No.: 19/034,712

(22) Filed: Jan. 23, 2025

(65) Prior Publication Data

US 2025/0305200 A1 Oct. 2, 2025

(30) Foreign Application Priority Data

Mar. 30, 2024 (IN) ............................ 202411026691

(51) Int. Cl.

| | |
|---|---|
| ***A61L 2/025*** | (2006.01) |
| ***A61L 2/10*** | (2026.01) |
| ***D06F 7/04*** | (2006.01) |
| ***D06F 19/00*** | (2006.01) |
| ***D06F 35/00*** | (2006.01) |
| *A61L 103/50* | (2026.01) |

(52) U.S. Cl.

CPC .............. *D06F 19/00* (2013.01); *A61L 2/025* (2013.01); *A61L 2/10* (2013.01); *D06F 7/04* (2013.01); *D06F 35/002* (2013.01); *A61L 2103/50* (2026.01); *A61L 2202/17* (2013.01)

(58) Field of Classification Search

None

See application file for complete search history.

(56) References Cited

U.S. PATENT DOCUMENTS

| | | | | |
|---|---|---|---|---|
| 2010/0326484 | A1 | 12/2010 | Wu | |
| 2019/0134242 | A1 | 5/2019 | Bonutti et al. | |
| 2022/0370654 | A1 * | 11/2022 | Ting | A61L 2/025 |
| 2023/0250570 | A1 | 8/2023 | Farakte et al. | |

FOREIGN PATENT DOCUMENTS

| | | |
|---|---|---|
| WO | 2006044951 A2 | 4/2006 |

OTHER PUBLICATIONS

Smilebrilliant; Professional Ultrasonic + UV Cleaner.

* cited by examiner

*Primary Examiner* — Levon J Shahinian

(74) *Attorney, Agent, or Firm* — Kendal M. Sheets

(57) ABSTRACT

The disclosure relates to a clothes pre-washing device. The clothes pre-washing device may include a washing tank. The washing tank includes a set of ultrasonic sensors, at least one inlet port, and an outlet port. Each ultrasonic sensor is integrated with an ultrasonic transducer configured for generating ultrasonic waves to create cavitation bubbles in a cleaning solution. Further, the at least one inlet port is controlled via one or more pumps that are configured for recirculating the cleaning solution. The clothes pre-washing device further include an ultrasonic generator coupled to the washing tank, configured for converting electric power into electrical signals to activate each of the ultrasonic transducer for generating the ultrasonic waves; and a top lid coupled to the washing tank configured to cover the washing tank. The top lid includes at least one ultraviolet-C light directed towards the washing tank.

14 Claims, 7 Drawing Sheets

CLOTHES PRE-WASHING DEVICE AND METHOD THEREOF

TECHNICAL FIELD

This disclosure relates generally to a home appliance, and more particularly to a clothes pre-washing device and a method thereof.

BACKGROUND

In recent years, washing machines have continued to undergo advancements in design, energy efficiency, and water-saving technologies. High-efficiency front-loading machines, top-loading machines, as well as compact and portable machine models, have gained popularity for their environmental benefits and space-saving characteristics. Several washing machines have been launched across the market that make use of electrolysis, ultrasonic, or cavitation techniques to promote the cleaning process or sanitization process for laundry. Typically, such washing machines include at least one wash cycle characterized as 'detergent-free' and which is designed for washing laundry that is relatively lightly soiled.

As washing machine manufacturers emphasize, the washing machines and stain removing devices that are currently available in the market are primarily designed for washing lightly soiled or stained clothes. However, for washing heavily soiled or stained clothes, the use of a surfactant-based detergent product continues to be necessary to achieve acceptable cleaning performance. In some cases, the stains are so stubborn that instead of using the surfactant-based detergent product they don't get removed from a cloth and a person has to clean the cloth manually to get rid of these stains. Moreover, washing machines parameters of the existing washing machines are more suited to a need of washing adult clothing. Also, operating a larger volume washing machine for small sized clothing (e.g., baby clothes, kitchen cleaning clothes, handkerchiefs, etc.) with frequent washing need doesn't serve the purpose efficiently.

Moreover, particularly for baby clothing and considering current demands of modern parenting lifestyles where clothes sanitization poses a significant contemporary concern for parents, there is pressing need within the market for technological innovations and solutions that address this concern. This is because currently existing washing machines could never achieve sufficient washing results for baby clothes because these washing machines are designed for adult cloth washing and requirements for washing baby clothes are very different. These washing machines lack functionalities for disposing common stains (such as poop, vomit, food substances, etc.), odor removal, faster and noiseless cycle, and the like, which are very specific to baby clothes laundry.

Hence, there remains a need for a comprehensive clothes pre-washing device that prewashes the baby clothes as well as small size clothes, offering a user-friendly interface, energy efficiency, noiseless, compact, and portable in size. Therefore, there is a need in the present state of art for a clothes pre-washing device.

SUMMARY

In an embodiment, a clothes pre-washing device is disclosed. The clothes pre-washing device may include a washing tank. The washing tank may include a set of ultrasonic sensors present at a periphery of the washing tank. It should be noted that each of the set of ultrasonic sensors may be integrated with an ultrasonic transducer configured for generating ultrasonic waves to create cavitation bubbles in a cleaning solution. The washing tank may further include at least one inlet port controlled via one or more pumps of a set of pumps. It should be noted that each of the set of pumps may be configured to recirculate the cleaning solution within the washing tank via a pumping technique. The washing tank may further include an outlet port present at a bottom surface of the washing tank. It should be noted that the outlet port may be coupled to a pipe including a pipe outlet to drain at least one of residual particles or the cleaning solution after a cleaning process. The clothes pre-washing device may further include an ultrasonic generator coupled to the washing tank, configured for converting electric power into electrical signals to activate each of the ultrasonic transducer for generating the ultrasonic waves. The clothes pre-washing device may further include a top lid coupled to the washing tank configured to cover the washing tank. It should be noted that the top lid may include at least one ultraviolet-C light directed towards the washing tank, configured to prevent accumulation of micro-organisms on clothes within the washing tank.

In another embodiment, a method of operating a clothes pre-washing device is disclosed. In one example, the method may include receiving a user selection corresponding to one or more actions associated with the clothes pre-washing device. It should be noted that the one or more actions may include powering the clothes pre-washing device, selecting a washing mode, selecting a hygiene mode, selecting an ultraviolet storage mode, and selecting one of a start option or a pause option for the clothes pre-washing device. The method may include initiating a cleaning process in response to receiving the user selection. To initiate the cleaning process, the method may further include generating, via an ultrasonic transducer including an ultrasonic sensor of a set of ultrasonic sensors, ultrasonic waves to create cavitation bubbles in a cleaning solution within a washing tank. The method to initiate the cleaning process may further include recirculating, via each of a set of pumps of the clothes pre-washing device, the cleaning solution within the washing tank via a pumping technique. The method may include detecting a completion of the cleaning process. The method may further include draining, via an outlet port of the clothes pre-washing device, at least one of residual particles or the cleaning solution, upon detecting the completion of the cleaning process.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Figure 1:
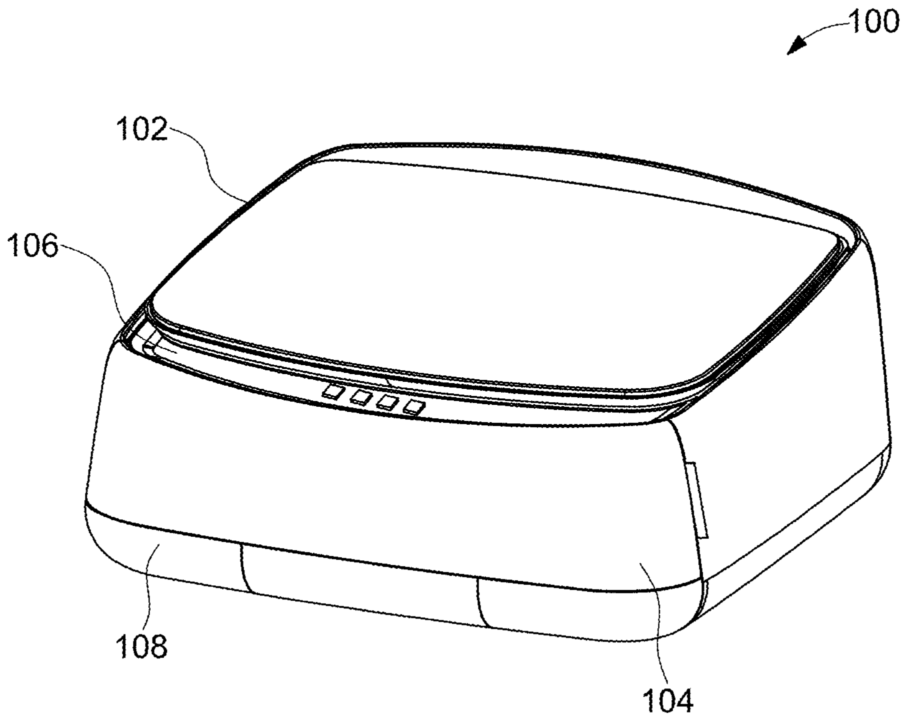
FIG. 1 illustrates an exemplary clothes pre-washing device, in accordance with some embodiments of the present disclosure.

Referring now to FIG. 1, an exemplary clothes pre-washing device 100 is illustrated, in accordance with some embodiments of the present disclosure. The clothes pre-washing device 100 may be configured to perform pre-washing of clothes based on user requirements. In other words, the user may utilize the clothes pre-washing device 100 to pre-wash the clothes to remove stubborn stains, dirt, odor, or any micro-organisms present on the clothes. In some embodiments, in order to perform pre-washing of the clothes, the clothes pre-washing device 100 may include a controller (not shown) (for example, a server, a processor, a microcontroller, a Computer Processing Unit (CPU), or any other computing device). The controller may be configured to operate the clothes pre-washing device 100 based on one or more actions performed by the user to pre-wash the clothes. Examples of a type of clothes that can be prewashed using the clothes pre-washing device 100 may be, but are not limited to baby clothes, kitchen cleaning clothes, handkerchief, socks, tie's, undergarments, or any other similar other small clothing item.

As depicted via the present FIG. 1, the clothes pre-washing device 100 may be a compact size and space saving device. In other words, the clothes pre-washing device 100 may be designed to be easily positioned on a top of a common front load washing machine or seamlessly fit into a washroom or any other place within a home environment taking up a minimal space. Further, as depicted via FIG. 1, the clothes pre-washing device 100 may include a top lid 102, a washing tank (not shown), an outer casing 104 configured to cover the washing tank, an interactive interface 106, and a feeding tray 108. The top lid 102 may be coupled to the washing tank. In particular, the top lid 102 may be configured to cover or uncover the washing tank. In other words, the top lid 102 may be opened and closed by the user to uncover or cover the washing tank, respectively, as and when required by the user. The user may open the top lid 102 to access the washing tank. For example, the user may open the top lid 102 for adding the clothes to the washing tank.

Further, the top lid 102 may include at least one ultraviolet-C light, such that the ultraviolet-C light may be directed towards the washing tank. In an embodiment, the at least one ultraviolet-C light may be configured to prevent accumulation of the micro-organisms on the clothes within the washing tank. In other words, the at least one ultraviolet-C light may prevent accumulation of the micro-organisms during pre-washing and storing the clothes in the washing tank of the clothes pre-washing device 100. In particular, the clothes when exposed to the at least one ultraviolet-C light may get sterilized by killing the micro-organisms, such as harmful molds, bacteria, virus, and any other similar micro-organism, from the clothes during the pre-washing and the storing, due to germicidal properties of the at least one ultraviolet-C light. By way of an example, the at least one ultraviolet-C light may easily kill the micro-organisms that are accumulated on the clothes of a baby or an infant, when the clothes gets exposed to the at least one ultraviolet-C light. By way of another example, the at least one ultraviolet-C light may be used to sterilize kitchen cleaning clothes, socks, undergarments, etc. In some embodiments, the at least one ultraviolet-C light may sterilize small toys (e.g., baby toys or pet toys) during pre-washing or storing.

Further, the washing tank may include a set of ultrasonic sensors (not shown), at least one inlet port (not shown), and an outlet (not shown). In an embodiment, each of the set of ultrasonic sensors may be present at a periphery of the washing tank. In particular, each of the set of ultrasonic sensors may be integrated with an ultrasonic transducer. Each ultrasonic transducer may be configured to generate ultrasonic waves (or ultrasonic vibrations) in the cleaning solution. The ultrasonic waves may create cavitation bubbles in the cleaning solution. In an embodiment, the ultrasonic waves generated by each ultrasonic transducer may be of a pre-defined ultrasonic frequency level (generally of higher frequencies) so that the created cavitation bubbles are small and concentrated to effectively remove dirt particles and stains from the clothes within the washing tank. As will be appreciated, the created cavitation bubbles may be small cavitation bubbles (e.g., microscopic bubbles) or voids that are formed in the cleaning solution when ultrasonic energy passes through it due to a rapid decrease in pressure. These cavitation bubbles implode with such force that contaminants (e.g., stains, micro-organisms, etc.) adhering to the clothes are dislodged. Moreover, these cavitation bubbles are microscopic in scale and cannot be seen during a cleaning process. Moreover, these cavitation bubbles are high-energy localized regions which can implode at high jet velocities. This is further depicted and explained in conjunction with FIG. 5.

Further, the at least one inlet port of the washing tank may be configured to dispense one of a pre-defined amount of clean water and a laundry product (e.g., one of a fabric cleaning product, a fabric softening product, or fabric sanitizing product) to fill the washing tank to clean the clothes during the cleaning process. As would be appreciated, a cleaning solution may be formed to initiate the cleaning process. The cleaning solution may be a mixture of the fabric cleaning product (e.g., a liquid laundry detergent, a powdered laundry detergent, or a tablet-based laundry detergent) and water. In some embodiments, apart from the fabric cleaning product, the mixture of the cleaning solution may include the fabric softening product, and the fabric sanitizing product, or any other similar fabric product that helps in maintenance of the clothes. In an embodiment, each of the at least one inlet port may be controlled via one or more pumps of a set of pumps. Further, each of the set of pumps may be configured to recirculate the cleaning solution within the washing tank via a pumping technique. As will be appreciated, the cleaning solution may be recirculated to effectively distribute the cavitation bubbles within the washing tank. This distribution of the cavitation bubbles may tackle blind spots and save energy.

Further, the outlet port may be present at a bottom surface of the washing tank. The outlet port may be configured to drain at least one of residual particles or the cleaning solution after the cleaning process. In an embodiment, the outlet port may be connected to a pipe. The pipe may include a pipe outlet configured to direct waste (i.e., the residual particles and the cleaning solution) towards a drainage port. This is further depicted and explained in conjunction with FIG. 3. In an embodiment, the outer casing 104 may be configured to cover all sides walls and a bottom wall of the washing tank. As depicted via present FIG. 1, a top surface of the outer casing 104 may include the interactive interface 106. The interactive interface 106 may be configured to perform the one or more actions. In other words, the user may use the interactive interface 106 to perform the one or more actions in order to pre-wash the clothes based on their preferences. The one or more actions, may include, but are not limited to, powering the clothes pre-washing device 100, selecting a washing mode, selecting a hygiene mode, selecting an ultraviolet storage mode, and selecting one of a start option or a pause option for the clothes pre-washing device 100. In order to perform the one or more actions, the interactive interface 108 may include a set of buttons, a washing mode selection button, a hygiene mode selection button, a storage mode selection button and a control button. This is further depicted and explained in conjunction with FIG. 7.

Further, the outer casing 104 of the washing tank 104 may include the feeding tray 108. The feeding tray 108 may be positioned within a cavity of the outer casing 104. The feeding tray 108 may include a set of sections. In an embodiment, the set of sections may be configured to store the fabric cleaning product, the fabric softening product, and the fabric sanitizing product. This is further depicted and explained in conjunction with FIG. 4.

Figure 2:
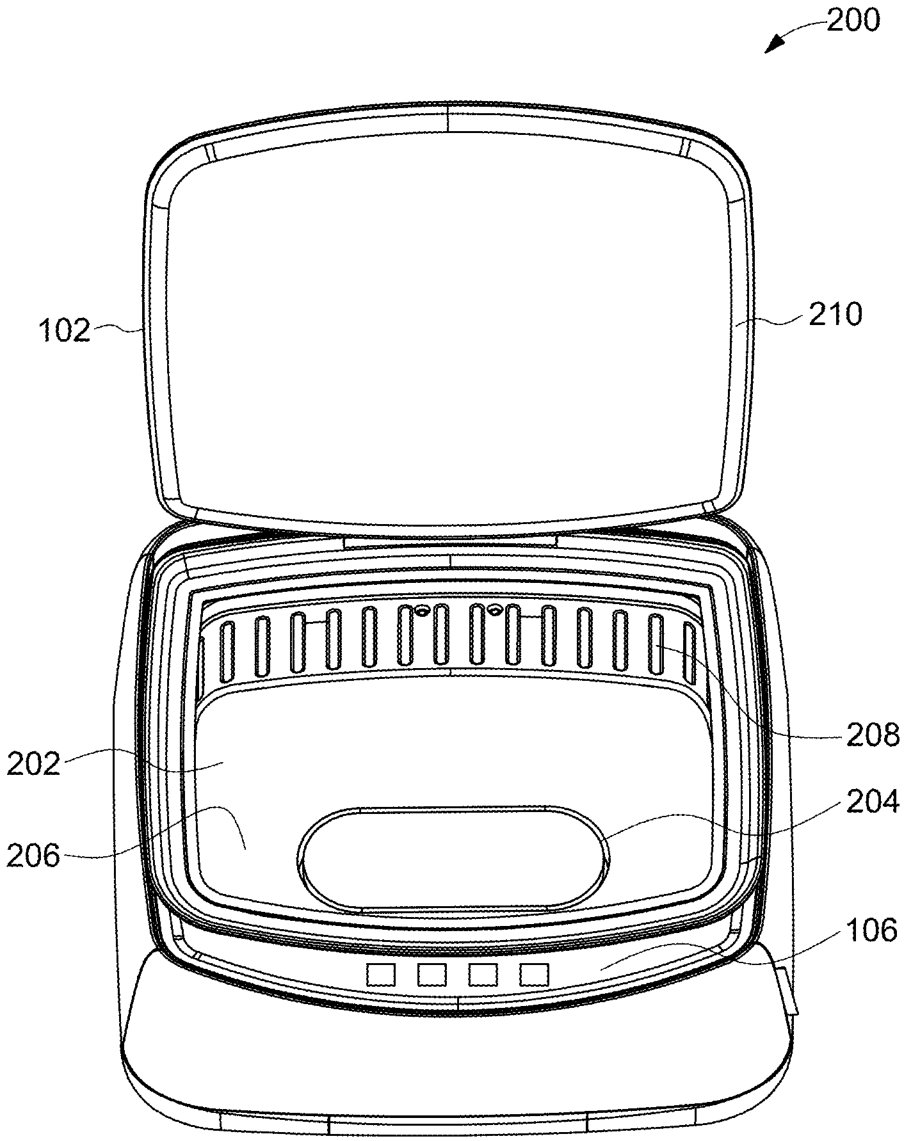
FIG. 2 illustrates an isometric view of a clothes pre-washing device, in accordance with some embodiments of the present disclosure.

Referring now to FIG. 2, an isometric view 200 of the clothes pre-washing device 100 is illustrated, in accordance with some embodiments of the present disclosure. FIG. 2 is explained in conjunction with FIG. 1. As depicted via the present FIG. 2, a washing tank 202 of the clothes pre-washing device 100 may be accessible by opening the top lid 102. In other words, the top lid 102 may be configured to move to an open position or a close position in order to uncover or cover the washing tank 202, respectively. By way of an example, the user of the clothes pre-washing device 100 may open the top lid 102 to access the washing tank 202. Upon opening the top lid 102, the user may add the clothes to the washing tank 202. After placing the clothes, the user may close the top lip 102 to cover the washing tank 202 in order to initiate the cleaning process.

Once the top lid 102 is closed, then the user may perform the one or more actions corresponding to the clothes pre-washing device 100. The one or more actions may include powering the clothes pre-washing device 100, selecting a washing mode, selecting a hygiene mode, selecting an ultraviolet storage mode, and selecting one of a start option or a pause option for the clothes pre-washing device 100. The one or more actions may be performed using the interactive interface 106. For this, the interactive interface 106 may include a set of buttons, e.g., a power button, a washing mode selection button, a hygiene mode selection button, a storage mode selection button, and a control button. The set of buttons available on the interactive interface 106 to enable the user to perform the one or more actions are further depicted and explained in conjunction with FIG. 7.

In one embodiment, the washing tank 202 may be configured to store the clothes that are soiled or stained for the pre-washing of the clothes. As will be appreciated, the washing tank 202 may be configured to hold a wash load (e.g., the soiled or the stained clothes) and the cleaning solution. In an embodiment, the washing tank 202 may be manufactured using stainless steel to resist erosion and corrosion of the washing tank 202. It should be noted that the manufacturing of the washing tank 202 is not limited to the use of the stainless steel. Apart from stainless steel any other similar material (e.g., Polypropylene (PP), Fiberglass Reinforced Plastic (FRP), Polyvinyl Chloride (PVC), or Chlorinated Polyvinyl Chloride (CPVC), etc.) may be used to manufacture the washing tank 202. Further, in order to reduce surface roughness and erosion of the washing tank 202, the washing tank 202 may be polished and coated using electro-polishing and titanium nitride (TiN) coating. As will be appreciated, the polishing and the coating of the washing tank 202 is not limited to these only. Apart from the electro-polishing and the TiN coating, any other similar material may be used to avoid the roughness and the erosion within the washing tank 202.

Further, as depicted via the present FIG. 2, the washing tank 202 may include an outlet port 204 inside side at a bottom surface 206. The outlet port 204 may be configured to drain at least one of the residual particles or the cleaning solution after the cleaning process. In an embodiment, the outlet port 204 may be connected to a pipe. The pipe may include a pipe outlet configured to direct waste (i.e., the residual particles and the cleaning solution) towards a drainage port. The drainage port may be further connected to a flexible pipe that may be configured to direct at least one of the residual waste or the cleaning solution to a drain area through the flexible pipe. Further, the washing tank 202 may include a plurality of equally spaced protrusions at a predefined distance (e.g., 2 centimeters). As depicted via the present FIG. 2, a protrusion from the plurality of equally spaced protrusions may correspond to a protrusion 208. In an embodiment, each of the plurality of equally spaced protrusions may be present at each inner side wall of the washing tank 202. The plurality of equally spaced protrusions may be configured to concentrate the ultrasonic waves towards a center of the washing tank 202. As will be appreciated, the plurality of equally spaced protrusions may enhance the cleaning process of the clothes and prevent damaging of the clothes.

Further, as depicted via the present FIG. 2, the top lid 102 may include at least one ultraviolet-C light. In an embodiment, the at least one ultraviolet-C light may be in a form of a single strip, e.g., an ultraviolet-C light 210. In some embodiments, the at least one ultraviolet-C light may be a combination of more than one ultraviolet-C light. As depicted via the present FIG. 2, the ultraviolet-C light 210 may be directed towards the washing tank 202. In other words, when the top lid 102 is in the closed position, the at ultraviolet-C light 210 may be facing the bottom surface 206 of the washing tank 202. The ultraviolet-C light 210 may be configured to prevent accumulation of the micro-organisms on the clothes within the washing tank 202. In an embodiment, the ultraviolet-C light 210 may be activated based on a user selection corresponding to the hygiene mode. In particular, the clothes when exposed to the ultraviolet-C light 210 may get sterilized by killing the micro-organisms, such as harmful molds, bacteria, virus, and any other similar micro-organisms, from the clothes during pre-washing and storing of the clothes due to germicidal properties of the ultraviolet-C light 210.

Figure 3:
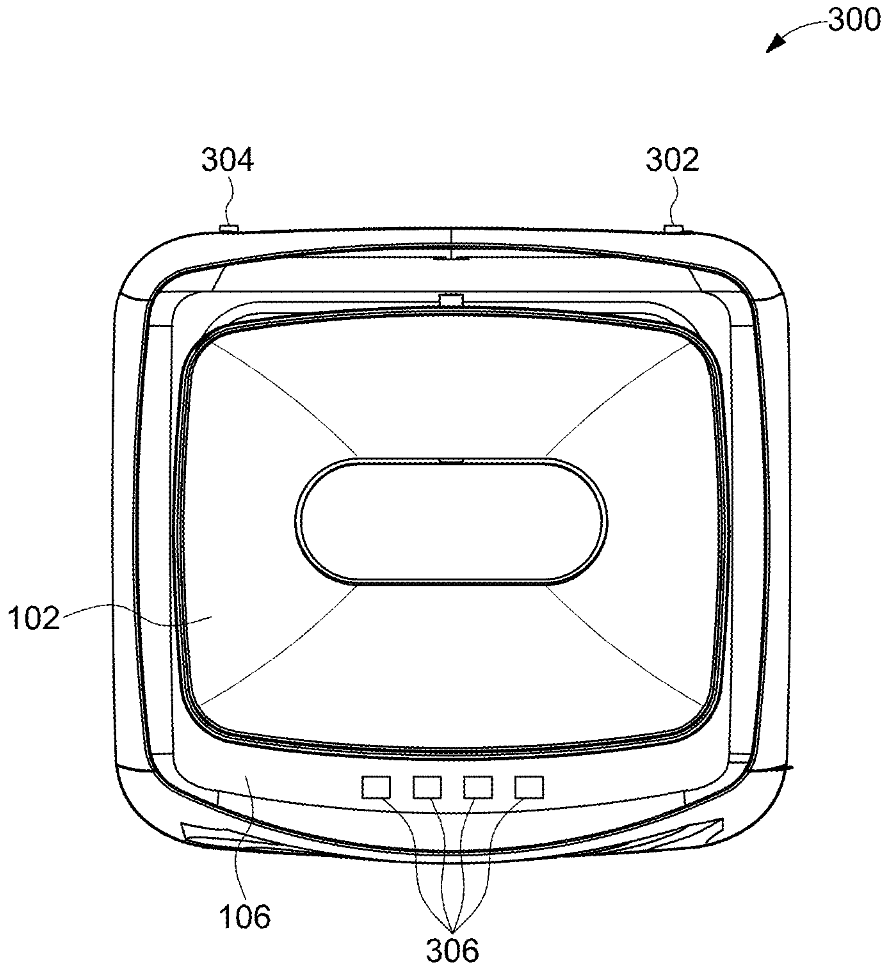
FIG. 3 illustrates a top view of a clothes pre-washing device, in accordance with some embodiments of the present disclosure.

Referring now to FIG. 3, a top view 300 of the clothes pre-washing device 100 is illustrated, in accordance with some embodiments of the present disclosure. FIG. 3 is explained in conjunction with FIGS. 1 and 2. As depicted via the top view 300, the top lid 102 of the clothes pre-washing device 100 is in the closed position. It should be noted that the top lid 102 may be made of a transparent or translucent material, e.g., a tempered glass. Further, as depicted via the top view 300, the clothes pre-washing device 100 may include a water inlet port 302 on one side (e.g., a right side) at a back portion of the clothes pre-washing device 100. In particular, the water inlet port 302 may be located on the outer casing 104 of the clothes pre-washing device 100. It should be noted that the water inlet port 302 may be present on a top edge of the back portion of the clothes pre-washing device 100. The water inlet port present 302 may be connected to each of the at least one inlet port of the washing tank 202. The water inlet port 302 may be configured to supply a pre-defined amount of water through the water inlet port 302 in the washing tank 104. It should be noted that the water inlet port 302 may be connected to external water source, e.g., a tap or a faucet.

Further, in order to drain at least one of the residual particles or the cleaning solution from the outlet port 204, the outlet port 204 may be coupled to the pipe that is connected to a drainage port 304 present on another side (e.g., a left side) opposite to the water inlet port 302. In other words, the pipe outlet of the pipe connected to the outlet port 204 may be connected to the drainage port 304. It should be noted that the drainage port 304 may be present on a bottom edge of the back portion of the clothes pre-washing device 100. The drainage port 304 may be further connected with the flexible pipe. Further, an outlet of the flexible pipe may be connected to the drain area to dispose of at least one of the residual particles or the cleaning solution. In particular, the residual particles or the cleaning solution may pass from the outlet port 204 through the pipe to the drainage port 304 via the pipe outlet. Further, at least one of the residual particles or the cleaning solution may be drained through the flexible pipe connected to the drainage port 304 in the drain area. Further, as depicted via the top view 300, the interactive interface 106 may include the set of buttons 306. The set of buttons 306 may include the power button, the washing mode selection button, the hygiene mode selection button, the storage mode selection button, and the control button. This is depicted and further explained in conjunction with FIG. 7.

Figure 4:
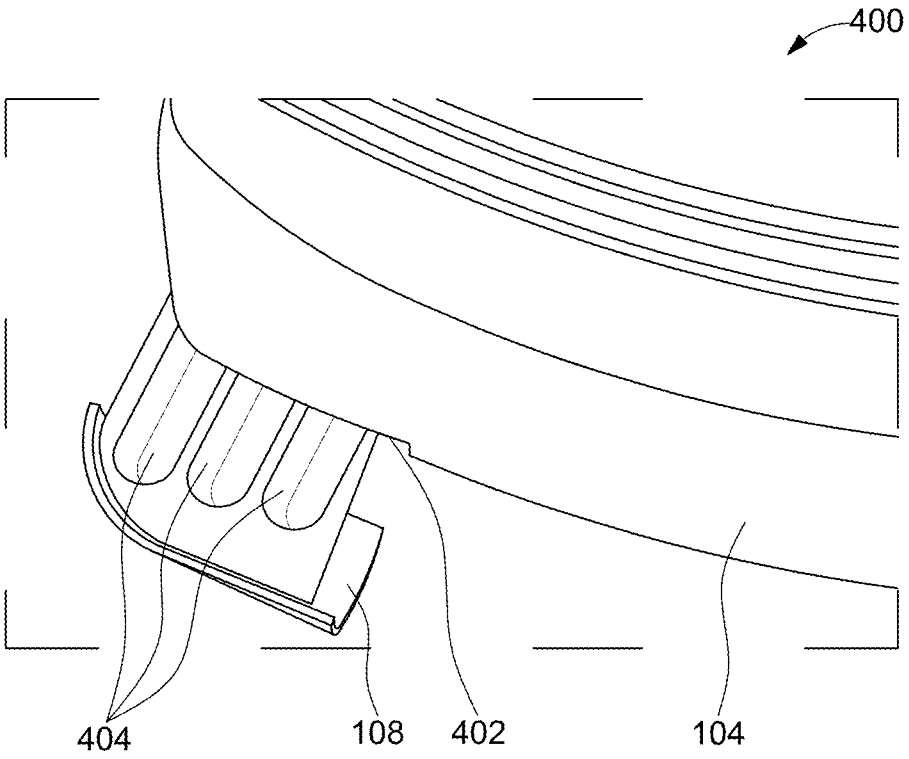
FIG. 4 illustrates an isometric view depicting a feeding tray of a clothes pre-washing device, in accordance with some embodiments of the present disclosure.

Referring now to FIG. 4, an isometric view 400 depicting a feeding tray 108 of the clothes pre-washing device 100 is illustrated, in accordance with some embodiments of the present disclosure. FIG. 4 is explained in conjunction with FIGS. 1, 2, and 3. As depicted via the present FIG. 4, the feeding tray 108 may be positioned within a cavity 402. The cavity 402 be formed within the outer surface 104 of the clothes pre-washing device 100. Further, as depicted via the present FIG. 4, the feeding tray 108 may slide out from the cavity 402. The feeding tray 108 may have a provision for the fabric cleaning product, the fabric softening product, and the fabric sanitizing product. In particular, the feeding tray 108 may include a set of sections. As depicted via the present FIG. 4, the set of sections may be a set of three sections 404. A section of the set of three sections 402 may be configured to store one of the fabric cleaning product, the fabric softening product, and the fabric sanitizing product. In other words, based on user requirements, the user may fill a first section with the fabric cleaning product, a second section with the fabric softening product, and a third section with the fabric sanitizing product.

As will be appreciated, the fabric cleaning product may be configured to remove the stains and dirt from the clothes. The fabric cleaning product may be any laundry cleansing agent, for example, a liquid laundry detergent, a powdered laundry detergent, or a tablet-based laundry detergent. The fabric softening product may be configured to soften fabric of the clothes. The fabric softening product may be any laundry softening agent, for example, a liquid fabric softener, a powder fabric softener, a fabric sheet softener, dryer balls, scented beads, a homemade fabric softener, and a bio-based fabric softener. Further, the fabric sanitizing product may be configured to neutralize the micro-organisms (e.g., molds, bacteria, viruses, etc.) present on the clothes for providing an extra layer of cleanliness to the clothes. The fabric sanitizing product may be any laundry disinfecting agent, for example, a chlorine bleach, an oxygen bleach, a pine oil disinfectant, a tea tree oil, and hydrogen peroxide.

Figure 5:
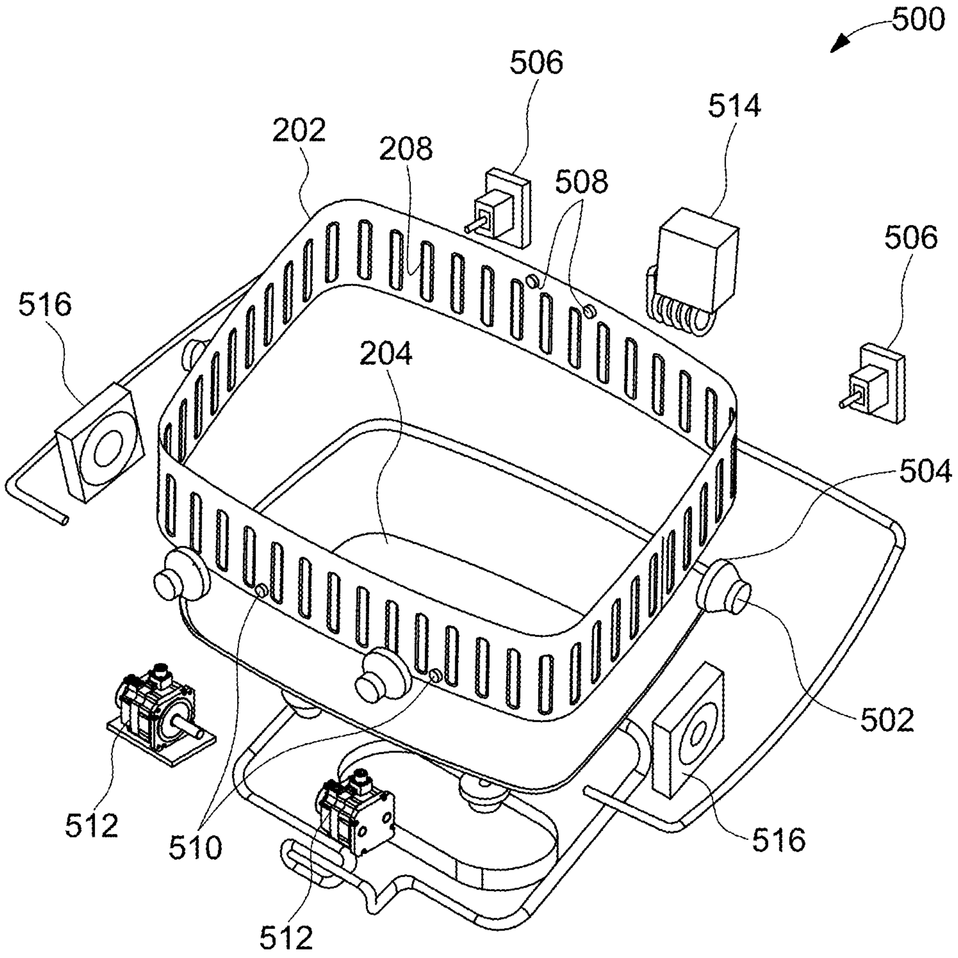
FIG. 5 illustrates an exploded view of a clothes pre-washing device, in accordance with some embodiments of the present disclosure.

Referring now to FIG. 5 an exploded view 500 of the clothes pre-washing device 100 is illustrated, in accordance with some embodiments of the present disclosure. FIG. 5 is explained in conjunction with FIGS. 1, 2, 3, and 4. The clothes pre-washing device 100 may include the washing tank 202. It should be noted that the washing tank 202 may be of a pre-defined capacity (e.g., 20 milliliters). As already explained in FIG. 3, the plurality of equally spaced protrusions (e.g., the protrusion 208) may be made at the pre-defined distance (e.g., 2 centimeters). In an embodiment, each of the plurality of equally spaced protrusions may be present at each inner side wall of the washing tank 202. In an embodiment, each of the plurality of equally spaced protrusions may be configured to effectively distribute the ultrasonic waves of higher ultrasonic frequency level in the cleaning solution. It should be noted that the ultrasonic waves may be generated of a pre-defined ultrasonic frequency level to operate the clothes pre-washing device 100 at the pre-defined ultrasonic frequency level based on a selected washing mode of the delicate washing mode, the normal washing mode, and the strong washing mode.

Further, the washing tank 202 may include the set of ultrasonic sensors present at the periphery of the washing tank 202. The set of ultrasonic sensors may be integrated with the ultrasonic transducer. For example, suppose a set of ten ultrasonic sensors (e.g., an ultrasonic sensor 502) may be coupled to the washing tank 202. For example, two ultrasonic sensors may be present on a front wall of the washing tank 202, two ultrasonic sensors on a back wall of the washing tank 202, two ultrasonic sensors on a bottom wall of the washing tank 202. Further, two ultrasonic sensor may be present on each side wall of the washing tank 202. It should be noted that each of the set of ten ultrasonic sensors may be present on an outer surface of the washing tank 202 and may be covered via the outer casing 104. Further, each of the set of ten ultrasonic sensors may include an ultrasonic transducer 504. In other words, a set of ten ultrasonic sensors may be integrated with a corresponding ultrasonic transducer of a set of ten ultrasonic transducers (e.g., the ultrasonic transducer 504) and are present on the periphery of the washing tank 202.

The set of ten ultrasonic sensors may be configured for generating the ultrasonic waves to create the cavitation bubbles in the cleaning solution. In particular, each of the set of ten ultrasonic sensors in conjunction with the corresponding ultrasonic transducer may be configured to generate ultrasonic waves which are sound waves with high frequency, in the cleaning solution. In other words, each of the set of ten ultrasonic sensors may be configured to generate ultrasonic vibration in the cleaning solution through mechanical energy coming from the corresponding ultrasonic transducer. Further, the set of ten ultrasonic sensors may be positioned in a way that ensures the clothes within the washing tank 202 are exposed to the ultrasonic waves from multiple directions and no blind spots areas are left within the washing tank 202 during the cleaning process. In an embodiment, the ultrasonic transducer 504 may be a piezoelectric ultrasonic transducer which converts electric energy into mechanical energy. The main advantage of using the piezoelectric ultrasonic transducer is their energy efficiency. This is due to direct conversion of the electrical energy into the mechanical energy, predominantly through lead zirconate titanate (PZT) or barium titanate materials. Energy loss from this conversion is minimal. Thus, around 95% of power generated using an ultrasonic generator (not shown) may be utilized for the cleaning process due to the direct conversion, resulting in an overall efficiency of the piezoelectric ultrasonic transducer approximately to 70% in any ultrasonic cleaning device.

In an embodiment, the ultrasonic generator may be coupled to the washing tank 202. Further, the ultrasonic generator may be configured to convert electric power into electrical signals to activate each of the set of ten ultrasonic transducers for generating the ultrasonic waves. In an embodiment, for effectively cleaning clothes (e.g., baby clothes), the ultrasonic generator may be configured to energize each of the set of ten ultrasonic transducers to generate the ultrasonic waves of higher ultrasonic frequency level (e.g., ranging between 60 kilohertz (kHz)-80 kHz). This may generate smaller cavitation bubbles for milder oscillations and implosions, effectively removing microscopic particles of the stains or the dirt, without causing damage to the clothes. As will be appreciated each of the set of ten ultrasonic sensors and the ultrasonic generator may be covered via the outer casing 104.

It should be noted that the cleaning solution may be nothing but a mixture of the fabric cleaning product and water. The mixture not only affects stains removal but also alters properties of the cleaning solution such as vapor pressure, surface tension, density, and viscosity, all of which influence vibration propagation and formation of cavitation bubbles during the cleaning process. Higher vapor pressure facilitates formation of the cavitation bubbles with less power input yet results in reduced energy absorption and release. In addition, elevated surface tension demands more energy for formation of the cavitation bubbles but enables greater energy storage within the cavitation bubbles. Further, circuit boards 506 (also referred to as electronic control boards) may be coupled to the washing tank 202. As already known to the person skilled in art, the circuit boards 506 may act as a central control unit that is configured for operating the washing tank 202.

Further the washing tank 202 may include the at least one inlet port. By way of an example, as depicted via the present FIG. 5, the at least one inlet port may correspond to a set of four inlet ports. The set of four inlet ports may include a pair of inlet ports 508 and a pair of inlet ports 510. The pair of inlet ports 508 may be present on a top edge of the back wall. In addition, the pair of inlet ports 510 be present on a bottom edge of the front wall. In an embodiment, each of the set of four inlet ports may receive water from a water inlet port (same as the water inlet port 302) of the clothes pre-washing device 100. Further, each of the set of four inlet ports may be controlled via the one or more pumps of the set of pumps. The set of pumps are configured for recirculating the cleaning solution within the washing tank 202 via the pumping technique. In an embodiment, the set of pumps may correspond to a set of two pumps (e.g., an exemplary pump 512). The pair of inlet ports 508 may be controlled via one pump of the set of two pumps and the pair of inlet ports 510 may be controlled via another pump of the set of two pumps. One pump near the pair of inlet ports 508 and the another pump near the pair of inlet ports 510 may recirculate the cleaning solution within the washing tank 202 to impart cycling wave effect for effective distribution of the ultrasonic waves and in turn to ensure maximum exposure of the cavitation bubbles to the clothes. As will be appreciated, each of the set of two pumps may be covered via the outer casing 104 of the clothes pre-washing device 100.

Further, the washing tank 202 may include the outlet port 204. The outlet port 204 may be coupled to the pipe. Further, the pipe outlet may be connected to a drainage port (same as the drainage port 304) present on the left side opposite the water inlet port. It should be noted that the drainage port may be present on the bottom edge of the back portion of the clothes pre-washing device 100. The drainage port may be further connected with the flexible pipe. Further, an outlet of the flexible pipe may be connected to the drain area to dispose of at least one of the residual particles or the cleaning solution.

Further, the washing tank 202 may include a heating system 514. The heating system 514 may be for heating the cleaning solution to a pre-defined temperature level based on the selected washing mode and the selected hygiene mode. As will be appreciated, a temperature of the cleaning solution significantly influences amount and intensity of the cavitation bubbles by altering properties of the cleaning solution. Increase in the temperature raises vapor pressure while reducing surface tension, viscosity, and density, fostering increased cavitation bubbles activity. Moreover, higher temperature enhances chemical activity, facilitating more efficient removal of the stains, dirt, and the microorganisms from the clothes like those soiled with pee, poop, food, vomit, etc. Further, higher temperature improves mass transport that further aids in dispersing and dissolving dirt particles, enhancing overall cleaning process. In addition, a ventilation fan 516 may be coupled to the washing tank 202. The ventilation fan 516 may be configured for assisting in dissipation of heat generated during the cleaning process, preventing overheating, and ensuring optimal performance and longevity of the clothes pre-washing device 100.

Figure 6:
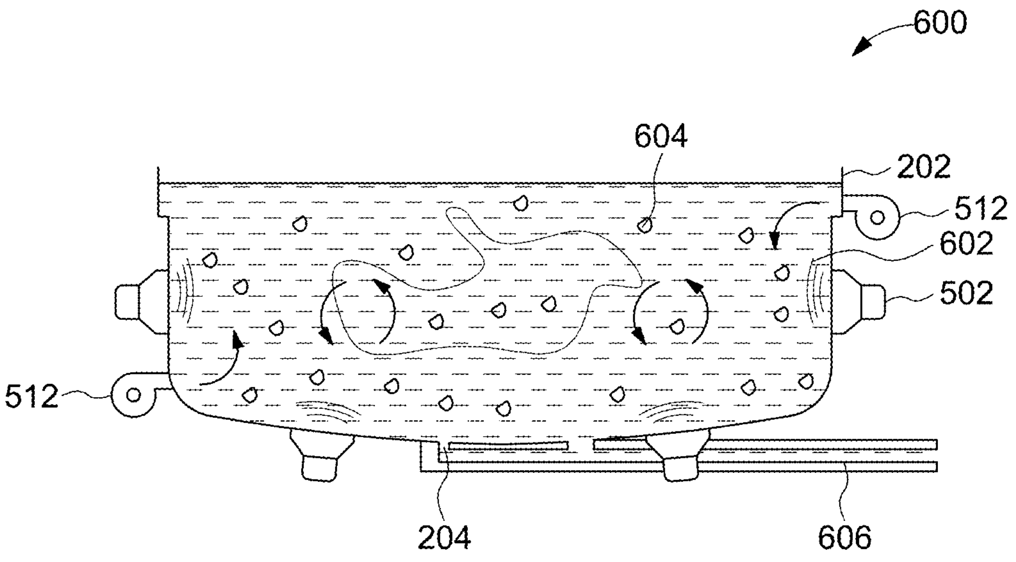
FIG. 6 illustrates a cross-sectional side view of a washing tank, in accordance with some embodiments of the present disclosure.

Referring now to FIG. 6, a cross-sectional side view 600 of the washing tank 202 is illustrated, in accordance with some embodiments of the present disclosure. FIG. 6 is explained in conjunction with FIGS. 1, 2, 3, 4, and 5. The cross-section side view 600 depicts a side view of the clothes pre-washing device 100. As depicted via the cross-section side view 600, when the washing tank may be filled with the cleaning solution, the set of ten ultrasonic sensors in conjunction with the corresponding ultrasonic transducer (e.g., the ultrasonic sensor 502 and the ultrasonic transducer 504) may be configured for generating the ultrasonic waves (i.e., an exemplary ultrasonic wave 602). As depicted via the cross-sectional view 600, each ultrasonic sensor may be configured for generating the ultrasonic waves of the predefined ultrasonic frequency level (i.e., of higher frequency). The ultrasonic waves may be generated to create cavitation bubbles (e.g., an exemplary cavitation bubble 604). The created cavitation bubbles may be smaller in size to easily remove the stains and the dirt from the clothes. Further, the small cavitation bubbles may be configured to implode on the clothes for removing the stains and dirt particles present on the clothes.

Further, the set of pumps associated may be associated with each of the at least one inlet port. As already explained in FIG. 5, each of a pair of inlet ports (i.e., the pair of inlet ports 508 and the pair of inlet ports 510) may be associated with a pump (e.g., the exemplary pump 512) of the set of two pumps. The pump may be configured to control each of the pair of inlet ports. Further, each pump may circulate the cleaning solution within the washing tank 202 as depicted via single arrows and circular arrows. The cleaning solution may be recirculated to effectively distribute the cavitation bubbles within the washing tank 202 to tackle blind spots. On completing the cleaning process, the outlet port 204 may be configured to drain out at least one of the residual particles and the cleaning solution through the pipe (e.g., an exemplary pipe 606). Further, the pipe outlet of the exemplary pipe 606 may be connected to the drainage port 304. The drainage port 304 may be further connected to the flexible pipe and the outlet of the flexible pipe may be connected to the drain area.

Figure 7:
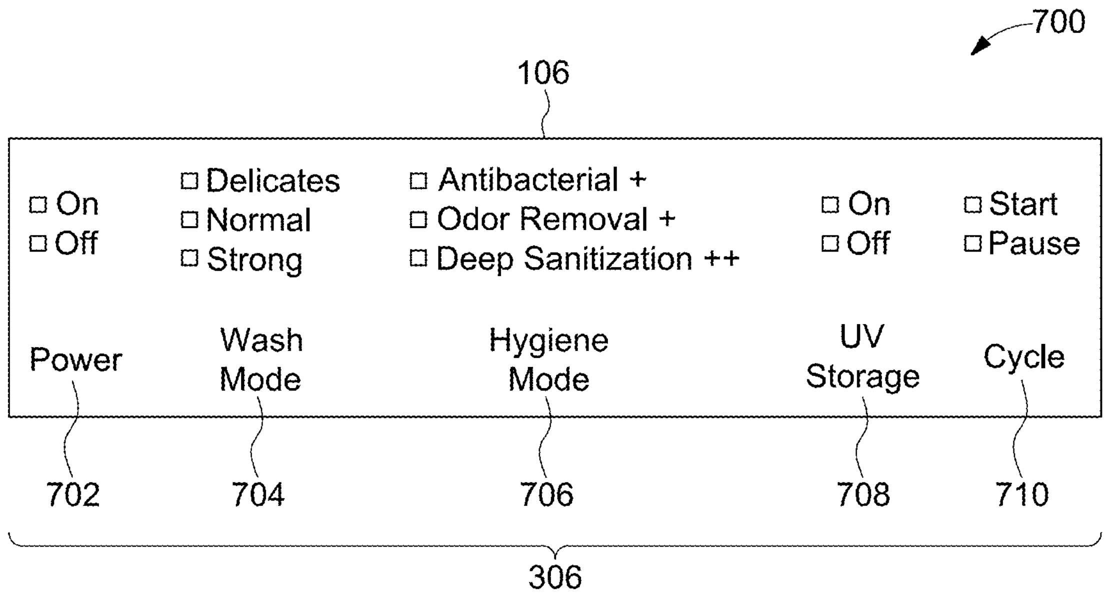
FIG. 7 illustrates an interactive interface of a clothes pre-washing device, in accordance with some embodiments of the present disclosure.

Referring now to FIG. 7, the interactive interface 106 of the clothes pre-washing device 100 is illustrated via a pictorial depiction 700, in accordance with some embodiments of the present disclosure. FIG. 7 is explained in conjunction with FIGS. 1, 2, 3, 4, 5, and 6. In an embodiment, the interactive interface 106 may be a capacitive interactive interface. It should be noted that the capacitive interactive interface may correspond to an interface that allows the user to interact with the clothes pre-washing device 100 through touch-sensitive controls. The interactive interface 106 may be used to operate the clothes pre-washing device 100. In particular, the user may use the interactive interface 106 to perform the one or more actions to operate the clothes pre-washing device 100. In order to operate the clothes pre-washing device 100, the interactive interface 106 may include the set of buttons 306.

It should be noted that each of the set of buttons 306 may be a touch button. In an embodiment, the one or more actions may include powering the clothes pre-washing device 100, selecting the washing mode, selecting the hygiene mode, selecting the ultraviolet storage mode, and selecting one of the start option or the pause option for the clothes pre-washing device 100. The washing mode may include one of the delicate washing mode, the normal washing mode, and the strong washing mode. The hygiene mode may include one of the antibacterial hygiene mode, the odor removal hygiene mode, and the deep sanitization hygiene mode.

As depicted via the present FIG. 7, the set of buttons 306 may include a power button 702, a washing mode selection button depicted as a wash mode button 704, a hygiene mode selection button depicted as a hygiene mode button 706, a storage mode selection button depicted as a ultraviolet (UV) storage button 708, and a control button depicted as a cycle button 710.

The power button 702 may be used for powering the clothes pre-washing device 100. In particular, once a power chord is connected to a power port, the user may use the power button 702 to turn 'on' or 'off' the clothes pre-washing device 100. The power button 702 in on condition may be supply electrical power to start the clothes pre-washing device 100. Further, the power button in off condition may stop supply of the electrical power to the clothes pre-washing device 100. Further, in present FIG. 7, a rectangular box shown adjacent to an 'on' and 'off' option on left side may be a visual indicator. The visual indicator may show a pre-defined color (e.g., a green color) when the clothes pre-washing device 100 is in on condition and a pre-defined color (e.g., a red color) when the clothes pre-washing device 100 is in off condition. In some embodiment, the 'on' or 'off' options may be a visual indicator that may illuminate upon a user selection.

Further, the wash mode button 704 may be used by the user to select one of the delicate washing mode, the normal washing mode, and the strong washing mode. When the user selects the delicate washing mode, a visual indicator depicted as a rectangular box adjacent to 'Delicates' may display a pre-defined color (e.g., green color) to indicate that an option 'Delicates' has been selected by the user. Similarly, when the user selects the normal washing mode, or the strong washing mode, then the visual indicator adjacent to 'Normal', or 'Strong', respectively, may get illuminated based on the user selection of the washing mode. In some embodiment, the 'Delicates', 'Normal', 'Strong' options may be a visual indicator that may illuminate based on the user selection of a corresponding washing mode.

In an embodiment, the clothes pre-washing device 100 may be configured to operate at the pre-defined ultrasonic frequency level and the pre-defined temperature level based on the selected washing mode of the delicate washing mode, the normal washing mode, and the strong washing mode. For example, in one embodiment, when the user selects the 'Delicates' option, a range of the pre-defined temperature level of the cleaning solution may be between 20 to 25 degrees in the delicate washing mode. Further, the pre-defined ultrasonic frequency level used for generating the ultrasonic waves may be between a range of 20 to 30 kHz.

In another embodiment, when the user selects the 'Normal' option, a range of the pre-defined ultrasonic frequency level of the cleaning solution may be between 30 to 35 degrees and a range of the pre-defined ultrasonic frequency level may be between 40 to 45 kHz in the normal washing mode. In yet another embodiment, when the user selects the 'Strong' option, a range of the pre-defined ultrasonic frequency level of the cleaning solution may be between 30 to 35 degrees and a range of the pre-defined ultrasonic frequency level may be between 50 to 60 kHz in the strong washing mode. It should be noted that the clothes pre-washing device 100 may be configured to operate for a pre-defined washing mode cycle time based on the selected washing mode. For example, for the delicate washing mode, the clothes pre-washing device 100 may operate for '15 minutes'. Similarly, for the normal washing mode and the strong washing mode, the clothes pre-washing device 100 may operate for '30 minutes' and '45 minutes', respectively. It should be noted that, the above-mentioned range of the pre-defined ultrasonic frequency level, the pre-defined temperature level, and the pre-defined washing mode cycle time for the selected washing mode are exemplary and may vary based on manufacturing requirements.

Further, the hygiene mode button 706 may be configured to select one of the antibacterial hygiene mode, the odor removal hygiene mode, and the deep sanitization hygiene mode. The user may select one of the antibacterial hygiene mode, the odor removal hygiene mode, and the deep sanitization hygiene mode by selecting a corresponding option, i.e., an 'antibacterial' option, an 'odor removal' option, and a 'deep sanitization' option, respectively. Further, based on a user selection of the corresponding option, a visual indicator adjacent to the corresponding option may be illuminated in the green color. In some embodiments, the corresponding option may itself get illuminated based on its selection. The clothes pre-washing device 100 may be configured to operate at a pre-defined ultraviolet-C exposure level, a pre-defined temperature level, and a pre-defined hygiene mode cycle time based on the selected hygiene mode of the antibacterial hygiene mode, the odor removal hygiene mode, and the deep sanitization hygiene mode.

For example, in one embodiment, when the user selects the 'antibacterial' option to select the antibacterial hygiene mode, the pre-defined temperature level for the cleaning solution may be between a range of 20 to 25 degrees, the pre-defined ultraviolet-C exposure level may be 250 nanometers, and the pre-defined hygiene mode cycle time may be 5 minutes. In another embodiment, when the user selects the 'odor removal' option to select the odor removal hygiene mode, the pre-defined temperature level for the cleaning solution may be between a range of 40 to 45 degrees, the pre-defined ultraviolet-C exposure level may be 280 nanometers, and the pre-defined hygiene mode cycle time may be between a range of 12 to 15 minutes. In yet another embodiment, when the user selects the 'deep sanitization' option to select the deep sanitization hygiene mode, the pre-defined temperature level for the cleaning solution may be between a range of 35 to 40 degrees, the pre-defined ultraviolet-C exposure level may be 270 nanometers, and the pre-defined hygiene mode cycle time may be between a range of 8 to 10 minutes. It should be noted that, the above-mentioned range of the pre-defined ultraviolet-C exposure level, the pre-defined temperature level, and the pre-defined hygiene mode cycle time for the selected hygiene mode are exemplary and may vary based on manufacturing requirements.

Further, the UV storage button 708 may be used by the user to turn 'on' or 'off' the ultraviolet storage mode for storing the clothes within the washing tank 202 when the ultraviolet-C light is turned on or off, respectively. It should be noted that, the visual indicator depicted via the rectangular box on left side that is adjacent to an 'on' or 'off' option may be configured to indicate whether the ultraviolet storage mode is on or off via a pre-defined color (e.g., the green color). Further, the cycle button 710 may be used by the user to start or pause the clothes pre-washing device 100. For example, the user may pause the clothes pre-washing device to add additional clothes. Once the additional clothes are added, the user may start the clothes pre-washing device 100. It should be noted that the visual indicator depicted via the rectangular box on left side that is adjacent to a corresponding start option and pause option may be configured to indicate whether the clothes pre-washing device 100 is running or paused, respectively. In some embodiments, these options 'on', 'off', 'start', 'pause' may be the visual indication itself and will get illuminated upon selection.

Figure 8:
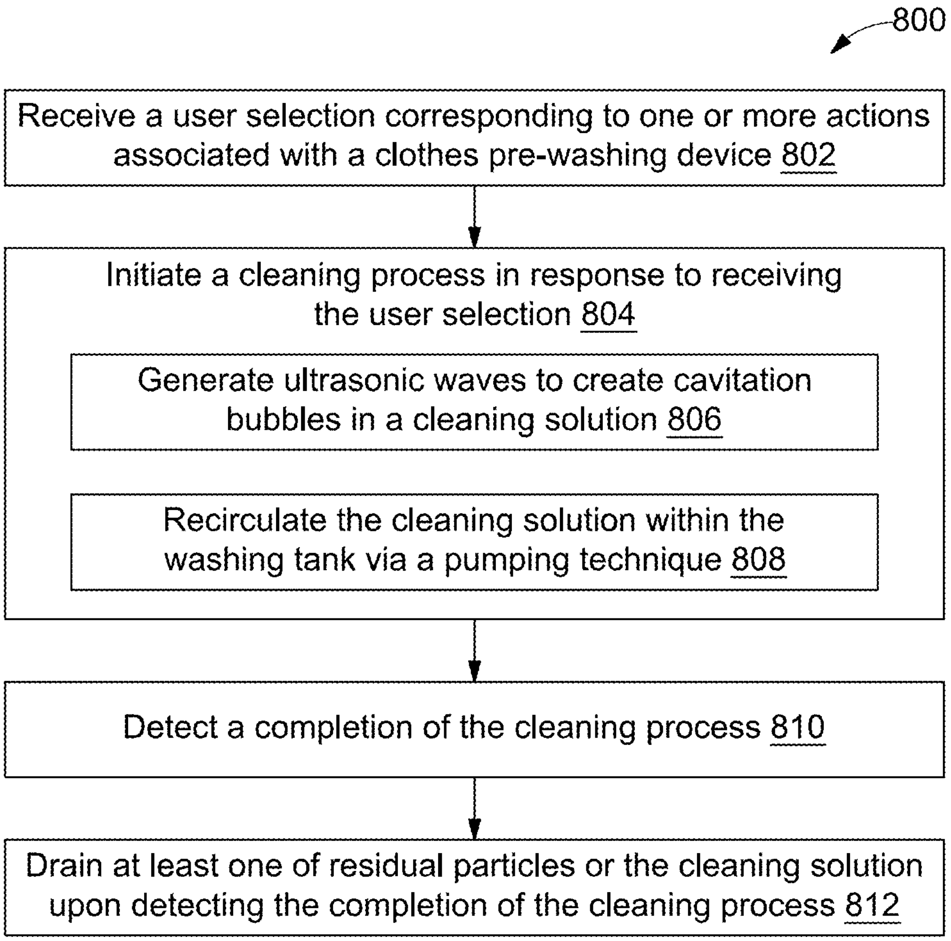
FIG. 8 illustrates a flowchart of a method of operating a clothes pre-washing device, in accordance with some embodiments of the present disclosure.

Referring now to FIG. 8, a method 800 of operating the clothes pre-washing device 100 is depicted via a flowchart, in accordance with some embodiments of the present disclosure. FIG. 8 is explained in conjunction with FIGS. 1, 2, 3, 4, 5, 6, and 7. At step 802, a user selection corresponding to one or more actions may be received. The one or more actions may be associated with the clothes pre-washing device 100. In an embodiment, the one or more actions may include powering the clothes pre-washing device 100, selecting a washing mode, selecting a hygiene mode, selecting an ultraviolet storage mode, and selecting one of a start option or a pause option for the clothes pre-washing device. In an embodiment, the washing mode may include one of a delicate washing mode, a normal washing mode, and a strong washing mode. Further, the hygiene mode may include one of an antibacterial hygiene mode, an odor removal hygiene mode, and a deep sanitization hygiene mode. With reference to FIG. 7, the user may perform the one or more actions via the set of buttons 306 present on the interactive display. To perform the one or more actions, initially, the user of the clothes pre-washing device 100 may place the clothes for pre-washing in the washing tank 202 by opening the top lid 102 of the clothes pre-washing device 100. Further, after placing the clothes, the user may close the top lid 102 to cover the washing tank 202.

Upon placing the clothes in the washing tank 202 the user may add at least one of the fabric cleaning product, the fabric softening product, or the fabric sanitizing product in the feeding tray 108 in a corresponding section of the set of sections. By way of an example, consider a scenario, where the user may want to pre-wash his infant clothes to remove stains of vomit, poop, etc., and kill any micro-organisms present on the clothes to disinfect the clothes for next use. In this scenario, once the user places the clothes within the washing tank 202, the user may turn 'on' the clothes pre-washing device 100 using the power button 702 upon connecting the power cord to the power port. Further, based on a type of the stains, the user may select an appropriate washing mode, e.g., the normal washing mode using the wash mode button 704. In addition, for disinfecting the clothes, the user may select an appropriate hygiene mode, e.g., the antibacterial hygiene mode using the hygiene mode button 706. Further, the user may turn 'off' the ultraviolet storage mode using the UV storage button 708 as he might not be interested in storing the clothes within the washing tank 202 after the cleaning process. Lastly, the user may start the cleaning process using the cycle button 710.

Further, upon receiving the user selection, each of the at least one inlet port may be configured to dispense a pre-defined amount of water as per the selected washing mode. In addition to dispensing the pre-defined amount of water, one or more inlet ports of the at least one inlet port may dispense the fabric cleaning product along with the pre-defined amount water to obtain the cleaning solution. The obtained cleaning solution may reach the pre-defined temperature level based on the selected washing mode and the selected hygiene mode. In continuation to the above example, for the normal washing mode, the range of the pre-defined temperature level of the cleaning solution may be between 30 to 35 degrees, and the range of the pre-defined ultrasonic frequency level may be between 40 to 45 kHz.

Further, in response to receiving the user selection, at step 804 a cleaning process may be initiated. To initiate the cleaning process, at step 806, ultrasonic waves may be generated in the cleaning solution. The ultrasonic waves may be generated to create cavitation bubbles in the cleaning solution within the washing tank 202. As will be appreciated, the ultrasonic waves may be generated by the ultrasonic transducer using each of the set of ultrasonic sensors. This has been already explained in FIG. 5. It should be noted that the ultrasonic waves may be generated of the pre-defined ultrasonic frequency level based on the selected washing mode. It should be noted that each of the selected washing mode and the selected hygiene mode may be configured to operate for the pre-defined amount of washing mode cycle time and the pre-defined amount of hygiene mode cycle time.

In addition to generation of the ultrasonic waves, at step 808, the cleaning solution may be recirculated within the washing tank 202 via the pumping technique. It should be noted that the cleaning solution may be circulated via the set of pumps. Further, at step 810, a completion of the cleaning process may be detected. Upon detecting the completing of the cleaning process, at step 812, at least one of residual particles or the cleaning solution may be drained. In an embodiment, the at least one of residual particles or the cleaning solution may be drained via the outlet port 204.

Further, after draining the residual particles and the cleaning solution, a pre-defined amount clean water may be dispensed based on the selected washing mode via each of the at least one inlet port. In some embodiments, in addition to the pre-defined amount of clean water, the fabric softening product and the fabric sanitizing product may be dispensed via the one or more inlet ports based on user requirement. Further, a mixture of the pre-defined amount of clean water including the fabric softening product and the fabric sanitizing product may be dispensed. Further, the ultraviolet-C light integrated on the top lid 102 of the washing tank 202 may be enabled for killing micro-organisms based on the selected hygiene mode.

As will also be appreciated, some of the above-described techniques may take the form of computer or controller implemented processes and apparatuses for practicing those processes. The disclosure can also be embodied in the form of computer program code containing instructions embodied in tangible media, such as floppy diskettes, solid state drives, CD-ROMs, hard drives, or any other computer-readable storage medium, wherein, when the computer program code is loaded into and executed by a computer or controller, the computer becomes an apparatus for practicing the invention. The disclosure may also be embodied in the form of computer program code or signal, for example, whether stored in a storage medium, loaded into and/or executed by a computer or controller, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

Various embodiments disclose a clothes pre-washing device. The disclosed clothes pre-washing device may include a washing tank. The washing tank may include a set of ultrasonic sensors present at a periphery of the washing tank. Each of the set of ultrasonic sensors may be integrated with an ultrasonic transducer configured for generating ultrasonic waves to create cavitation bubbles in a cleaning solution. Further, the washing tank may include at least one inlet port controlled via one or more pumps of a set of pumps. Each of the set of pumps may be configured to recirculate the cleaning solution within the washing tank via a pumping technique. In addition, the washing tank may include an outlet port present at a bottom surface of the washing tank. The outlet port may be coupled to a pipe comprising a pipe outlet to drain at least one of residual particles or the cleaning solution after a cleaning process. Further, the disclosed clothes pre-washing device may include an ultrasonic generator coupled to the washing tank, configured for converting electric power into electrical signals to activate each of the ultrasonic transducer for generating the ultrasonic waves. Furthermore, the disclosed clothes pre-washing device may include a top lid coupled to the washing tank configured to cover the washing tank. The top lid may include at least one ultraviolet-C light directed towards the washing tank, configured to prevent accumulation of micro-organisms on clothes within the washing tank.

Thus, the present disclosure may overcome drawbacks of traditional problem of manually pre-washing clothes for removing stubborn stains and performing sanitization of clothes. The present disclosure discloses a clothes pre-washing device that may provide convenience to a user by automating a process of manually pre-washing certain clothes, particularly of their babies that have hardened stains of baby's poop, food, vomit, etc. This may reduce parents' fatigue and eliminate uneasiness felt during manual removal of these hardened stains. Further, the disclosed clothes pre-washing device enables the users to sanitize delicate clothes of their babies with care and maintain good hygiene. In addition, the disclosed clothes pre-washing device may loosen up stubborn stains and pre-treat the clothes before a washing cycle to sustain quality of the clothes. In addition, the disclosed clothes pre-washing device may reduce baby cloth laundry time as compared to manual cleaning process and pre-washes multiple clothes in one go, thus relieving the user from frequent washing needs. Further, the disclosed clothes pre-washing device may be configured to work silently and also offers hygienic storage option for the clothes.

In light of the above-mentioned advantages and the technical advancements provided by the disclosed method and device, the claimed steps as discussed above are not routine, conventional, or well understood in the art, as the claimed steps enable the following solutions to the existing problems in conventional technologies. Further, the claimed steps clearly bring an improvement in the functioning of the device itself as the claimed steps provide a technical solution to a technical problem.

The specification has described a clothes pre-washing device and method thereof. The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, non-volatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A clothes pre-washing device comprising:
 a washing tank comprising:
  a set of ultrasonic sensors present at a periphery of the washing tank, wherein each of the set of ultrasonic sensors are integrated with an ultrasonic transducer configured for generating ultrasonic waves to create cavitation bubbles in a cleaning solution;
  at least one inlet port controlled via one or more pumps of a set of pumps, wherein each of the set of pumps are configured to recirculate the cleaning solution within the washing tank via a pumping technique; and
  an outlet port present at a bottom surface of the washing tank, wherein the outlet port is coupled to a pipe comprising a pipe outlet to drain at least one of residual particles or the cleaning solution after a cleaning process;
 an ultrasonic generator coupled to the washing tank, configured for converting electric power into electrical signals to activate each of the ultrasonic transducer for generating the ultrasonic waves; and
 a top lid coupled to the washing tank configured to cover the washing tank, wherein the top lid comprises at least one ultraviolet-C light directed towards the washing tank, configured to prevent accumulation of micro-organisms on clothes within the washing tank.

2. The clothes pre-washing device of claim 1, wherein the washing tank comprises a plurality of equally spaced protrusions at a pre-defined distance.

3. The clothes pre-washing device of claim 1, wherein the set of ultrasonic sensors are mounted on each of a side wall and a bottom wall of the washing tank.

4. The clothes pre-washing device of claim 1, further comprising an interactive interface, wherein the interactive interface comprising:
 a set of buttons for performing one or more actions, wherein a set of buttons comprises a power button, a washing mode selection button, a hygiene mode selection button, a storage mode selection button, and a control button.

5. The clothes pre-washing device of claim 4, wherein the one or more actions comprises powering the clothes pre-washing device, selecting a washing mode, selecting a hygiene mode, selecting an ultraviolet storage mode, and selecting one of a start option or a pause option for the clothes pre-washing device.

6. The clothes pre-washing device of claim 5, wherein the washing mode comprises one of a delicate washing mode, a normal washing mode, and a strong washing mode.

7. The clothes pre-washing device of claim 6, wherein the clothes pre-washing device is configured to operate at a pre-defined ultrasonic frequency level and a pre-defined temperature level based on a selected washing mode of the delicate washing mode, the normal washing mode, and the strong washing mode.

8. The clothes pre-washing device of claim 5, wherein the hygiene mode comprises one of an antibacterial hygiene mode, an odor removal hygiene mode, and a deep sanitization hygiene mode.

9. The clothes pre-washing device of claim 8, wherein the clothes pre-washing device is configured to operate at a pre-defined ultraviolet-C exposure level, a pre-defined temperature level, and a pre-defined hygiene mode cycle time based on a selected hygiene mode of the antibacterial hygiene mode, the odor removal hygiene mode, and the deep sanitization hygiene mode.

10. The clothes pre-washing device of claim 5, further comprising a heating system configured for heating the cleaning solution to the pre-defined temperature level based on the selected washing mode and the selected hygiene mode.

11. The clothes pre-washing device of claim 1, further comprising:
 a feeding tray comprising a set of sections, wherein a section of the set of sections is configured for storing one of a fabric cleaning product, a fabric softening product, and a fabric sanitizing product.

12. A method of operating a clothes pre-washing device, the method comprising:
 receiving, by the clothes pre-washing device, a user selection corresponding to one or more actions associated with the clothes pre-washing device, wherein the one or more actions comprises powering the clothes pre-washing device, selecting a washing mode, selecting a hygiene mode, selecting an ultraviolet storage mode, and selecting one of a start option or a pause option for the clothes pre-washing device;
 initiating, by the clothes pre-washing device, a cleaning process in response to receiving the user selection, wherein the initiating the cleaning process comprises:
  generating, via an ultrasonic transducer integrated within each of a set of ultrasonic sensors, ultrasonic waves to create cavitation bubbles in a cleaning solution within a washing tank;
  recirculating, via each of a set of pumps of the clothes pre-washing device, the cleaning solution within the washing tank via a pumping technique;
 detecting, by the clothes pre-washing device, a completion of the cleaning process; and
 draining, via an outlet port of the clothes pre-washing device, at least one of residual particles or the cleaning solution upon detecting the completion of the cleaning process.

13. The method of claim 12, wherein the washing mode comprises one of a delicate washing mode, a normal washing mode, and a strong washing mode.

14. The method of claim 12, wherein the hygiene mode comprises one of an antibacterial hygiene mode, an odor removal hygiene mode, and a deep sanitization hygiene mode.

* * * * *